United States Patent [19]

Lorenz

[11] Patent Number: 5,306,504
[45] Date of Patent: Apr. 26, 1994

[54] SKIN ADHESIVE HYDROGEL, ITS PREPARATION AND USES

[75] Inventor: Donald H. Lorenz, Basking Ridge, N.J.

[73] Assignee: Paper Manufactures Company, Philadelphia, Pa.

[21] Appl. No.: 987,642

[22] Filed: Dec. 9, 1992

[51] Int. Cl.$^5$ ............................................. A61F 13/00
[52] U.S. Cl. .................... 424/449; 424/401; 424/443; 424/445; 424/448; 424/486; 424/487; 514/781; 514/789; 514/946; 604/307; 602/48
[58] Field of Search ............... 424/443, 445, 448, 449, 424/401, 486, 487

[56] References Cited

U.S. PATENT DOCUMENTS

| | | | |
|---|---|---|---|
| 3,336,129 | 8/1967 | Herret et al. | 71/92 |
| 3,545,230 | 12/1970 | Morse | 62/530 |
| 3,664,343 | 5/1972 | Assarsson | 128/284 |
| 3,759,880 | 9/1973 | Hoffmann et al. | 260/803 R |
| 3,878,175 | 4/1975 | Steckler | 260/78.5 BB |
| 3,993,049 | 11/1976 | Kater | 128/206 E |
| 4,078,568 | 3/1978 | Etes et al. | 128/283 |
| 4,094,822 | 6/1978 | Kater | 252/512 |
| 4,226,247 | 10/1980 | Hauser et al. | 128/641 |
| 4,499,896 | 2/1985 | Heinecke | 128/156 |
| 4,646,730 | 3/1987 | Schonfeld et al. | 128/156 |
| 4,750,482 | 6/1988 | Sieverding | 128/156 |
| 5,156,601 | 11/1992 | Lorenz et al. | 128/156 |

OTHER PUBLICATIONS

H. P. Frank, "The Lactam-Amino Acid Equilibra for Ethylpyrrolidone and Polyvinypyrrolidone", *J. Poly Sci,* 12, 565-576 (1954).

A. Conix and G. Smets, "Ring Opening in Lactam Polymers", *Journal of Polymer Science,* XV, 221-229 (1955).

*Primary Examiner*—Thurman K. Page
*Assistant Examiner*—Jyothsna Venkat
*Attorney, Agent, or Firm*—Howson and Howson

[57] ABSTRACT

A skin adhesive hydrogel formed by mixing in aqueous medium: (A) major proportion of a high molecular weight water-soluble polyvinylpyrrolidone having ring opened pyrrolidone groups and (B) a minor proportion of a water-soluble multifunctional amine-containing polymer to form a water insoluble, water swellable cross-linked salt between carboxyl groups of the ring opened pyrrolidone groups and basic amine groups of the polyfunctional amine-containing polymer. The reaction is advantageously carried out in the presence of a plasticizer.

22 Claims, No Drawings

SKIN ADHESIVE HYDROGEL, ITS PREPARATION AND USES

The present invention relates to adhesive hydrogel compositions based on a cross-linked polyvinylpyrrolidone, for use on animal bodies, particularly human bodies. Examples of such uses include surgical drapes, wound and burn dressings and packings, bandages, plasters, transdermal and iontophoresis drug delivery systems, antimicrobial barriers for catheter hubs, ostomy products, electrodes, face masks and nail wraps. The invention also relates to the method of making the hydrogel and to medical and cosmetic systems or devices comprising the hydrogel.

BACKGROUND OF THE INVENTION

The use of a cross-linked polyvinylpyrrolidone hydrogel as an adhesive in one or more of the foregoing applications is known. The principal means of cross-linking the polyvinylpyrrolidone (PVP) has been by ionizing radiation. Typical U.S. Pat. Nos. directed to this are: 4,646,730 to Schonfeld et al; 4,750,482 to Sieverding, and 3,545,230 to Morse. Chemically cross-linked PVP and copolymers of PVP and other materials are also disclosed for one or more of the aforementioned applications in, for example, the following U.S. Pat. Nos.: 3,759,880 to Hoffmann et al.; 3,878,175 to Steckler; 3,336,129 to Herrett et al.; 4,094,822 to Kater; 3,993,049 to Kater, and 4,498,896 to Heinecke.

It is the principal object of the present invention to provide an improved skin adhesive hydrogel composition based on polyvinylpyrrolidone.

It is another object of the present invention to provide a skin adhesive hydrogel based on cross-linked polyvinylpyrrolidone but not requiring the use of ionizing radiation in its preparation.

It is still another object of the present invention to provide a skin adhesive hydrogel composition based on cross-linked polyvinylpyrrolidone but having certain advantages over prior such hydrogel compositions.

These and other objects, including the provision of a method for preparing the improved hydrogel composition and the provision of improved medical and cosmetic systems comprising the hydrogel will become apparent from a consideration of the following specification and claims.

SUMMARY OF THE INVENTION

The skin adhesive hydrogel composition of the present invention is prepared by mixing in aqueous medium:

A. a water-soluble high molecular weight polyvinylpyrrolidone having ring opened pyrrolidone groups providing at least $1.5 \times 10^{-2}$ milliequivalents of carboxylic acid groups per gram of polymer, and B. a water-soluble multifunctional amine-containing polymer, until reaction between acid groups of the ring-opened polyvinylpyrrolidone and basic amine groups of the multifunctional amine-containing polymer to form a water-insoluble, water-swellable cross-linked ampholyte salt.

The resulting hydrogel composition, therefore, comprises a water-insoluble, water-swellable cross-linked ampholyte salt of A. a water-soluble high molecular weight polyvinylpyrrolidone having ring opened pyrrolidone groups providing at least $1.5 \times 10^{-2}$ milliequivalents of carboxylic acid groups per gram of polymer, and B. a water-soluble multifunctional amine-containing polymer.

It will be noted that the above-described cross-linking does not require ionizing radiation. This in itself is a significant advantage. Moreover, since the cross-linking involves chemical reaction, the cross-linking is strong and can be accomplished in the presence of high electrolyte content to make conductive gels, iontophoresis devices, and the like.

DESCRIPTION OF THE PREFERRED EMBODIMENTS

Referring to the polyvinylpyrrolidone starting material, it will contain at least a stated minimum of carboxylic acid groups due to ring opening (hydrolysis). Ring opening of pyrrolidone groups on polyvinylpyrrolidone was reported by H. P. Frank in the *Journal of Polymer Science* 12, 565–576 (1954). G. Smets and A. Comex showed that an equilibrium was formed in ring opening reactions in the *Journal of Polymer Chemistry*, 13, 221–229 (1955). The ring opened PVP will provide at least $1.5 \times 10^{-2}$ milliequivalents of carboxylic acid groups per gram of PVP. Higher levels give a greater number of cross links. The level should not be so high as to result in significant cross-linking of the PVP with itself. Some commercial polyvinylpyrrolidone is available already containing the requisite amount of opened pyrrolidone rings. Others do not and these can be treated in aqueous solution at elevated temperature with a weak acid, such as acetic acid, or a base, such as sodium hydroxide, until the desired degree of ring opening has been achieved. The PVP will have a high molecular weight, with a preferred K-value of at least about 50. It is possible that the K-value could go as low as about 30 if sufficient rings are opened to provide the gel-forming cross-linking reaction described herein. While there is likely no upper limit to the K-value of the PVP as far as the present invention is concerned, K-120 is about as high as available commercially. Thus, the K-value will generally not exceed about 120. As is well known, K-values as assigned to PVP represent a function of the average molecular weight. They are derived from viscosity measurements and are calculated according to Fikentscher's formula.

The multifunctional amine-containing polymer is a water-soluble polymer containing basic amine groups available for salt formation with the carboxyl groups of the ring opened polyvinylpyrrolidone. Examples are polyethyleneimine, amine terminated polyethylene oxide polymers, amine terminated polyethylene/polypropylene oxide polymers, polymers and copolymers of dimethyl amino ethyl methacrylate, and vinyl pyrrolidones, and the like.

The preparation of the hydrogel takes place in aqueous medium, with a water content of from about 40 to about 80%, by weight. This is most easily accomplished by mixing aqueous solutions of the ring opened PVP and of the multifunctional amine-containing polymer. The temperature does not appear to be critical, and the reaction is conveniently carried out at room temperature. Upon mixing, a water insoluble gel is formed. The gel is not soluble in excess added water but does swell further.

The proportions of ring opened PVP to multifunctional amine-containing polymer may vary widely. Generally, however, the proportion, by weight, of the former to the latter is between about 15:1 to about 40:1.

It appears that, as the result of the reaction, a salt is formed between two or more molecules of ring opened PVP and the multifunctional amine containing polymer according to the following (using the preferred polyethyleneimine as illustrative of the multifunctional amine-containing polymer):

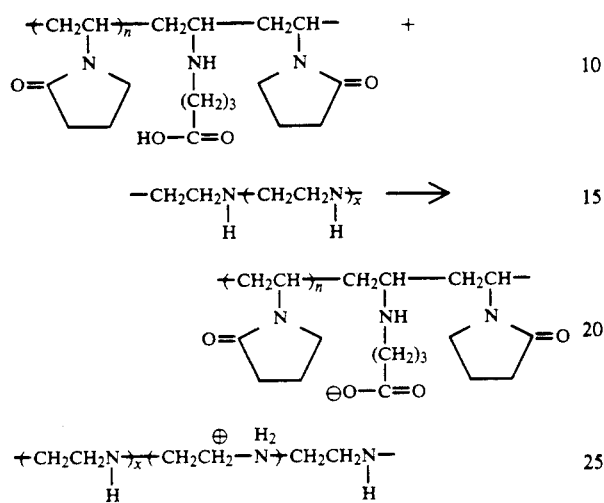

Inasmuch as it is preferred to include a plasticizer for the gel in the hydrogel composition, especially for tack development, such a plasticizer is advantageously included in the reaction medium. The plasticizer will be water soluble to provide a clear gel and not so hydrophobic as to decrease tack. Examples of such plasticizers are glycerine and polyethylene glycol, particularly polyethylene glycol 300. The plasticizer may be present in an amount between about 20 and about 55%, by weight, based on the combined weight of the cross-linked PVP and the plasticizer. The degree of tack increases as the amount of plasticizer increases, however, the strength of the gel (adherence to itself) decreases at a plasticizer content above about 25%.

As will appear hereinafter other agents serving as components adapted to impart a desired medical or cosmetic result may be included in the reaction mixture initially or combined with the hydrogel product subsequently.

The hydrogel product may also contain a phospholipid surfactant that provides some antibacterial stabilizing properties and helps to disperse other materials in the aqueous gel.

The hydrogel product of the present invention is useful in a wide variety of systems involving application to animal bodies, including especially human bodies. These include medical systems such as an adhesive for surgical drapes, wound and burn dressings and packings, bandages, plasters, transdermal and iontophoresis drug delivery devices, antimicrobial barriers for catheter hubs and electrodes. These uses also include cosmetic systems where it may be used as an adhesive for nail wraps or for its skin hydrating ability in hydrating face masks.

In a wound or burn dressing or packing, for example, in addition to the incorporation of a plasticizer and surfactant in the gel, the product may also contain a bactericide such as chlorhexidine gluconate, silver or copper compounds like silver sulfadiazine, silver apacide and copper apacide, or an antibiotic or antimicrobial. The gel composition may also contain enough sodium chloride to match physiological saline in order to prevent osmotic pumping from the wound, and agents to promote regrowth of tissue. Wound or burn dressings and packings generally involve a releasable thermally formed plastic receptacle for holding the hydrogel, and a polymeric film, such as polyurethane film, backing to control moisture-vapor transmission.

The tacky hydrogel may be used to attach a medical device to the body. In this case the aqueous gel may contain, in addition to the tackifying plasticizer, an antimicrobial agent. When used as an adhesive to attach an catheter, such as a central venous catheter or intravenous catheter, it covers the hub providing an antimicrobial barrier to infection. The tacky gel may also be used to attach ostomy products to the body.

An electrolyte salt may be included in the aqueous gel to render it conductive for use in attaching electrocardiogram electrodes, transcutaneous electrical nerve stimulator electrodes, electro-surgical unit electrodes, bio-feedback electrodes and iontophoresis drug delivery electrodes and defibrillation pads. Potassium chloride and magnesium acetate are examples of suitable electrolyte salts. Such salts may be present in the aqueous gel in an amount between about 1 and about 20%, by weight, preferably between about 5 and about 10%. The electrolyte salt may be incorporated in the reaction mixture at or about the time that the ring opened PVP and multifunctional amine containing polymer are mixed, preferably as by adding it to the water prior to dissolving the ring opened PVP. The conductive hydrogel may also contain bioeffective material for iontophoresis drug delivery.

In a transdermal drug delivery system, the hydrogel of the present invention will contain, in addition to the plasticizer, skin absorption agents like alcohols and amides, and at least one bioeffecting drug. Examples of drugs that may be incorporated in such a system are nitroglycerine, pilocarpine, scopolamine, clonidine, fentanyl, nicotine, fenfluramine, phenterimine, phenylpropanolamine, theophylline, lidocaine, benzocaine, capsaicin, nicotinates, ergotamine tartrate, miconazole nitrate, salicylates such as choline salicylate, methyl salicylate, and the like. Such drugs may be added to the hydrogel in an amount up to about 10%, by weight.

Other applications for the hydrogel of the present invention are in cosmetics, as for hydrating face masks and nail wraps. The hydrogel, because of its high water content may be used to hydrate the skin and provide a cooling effect. The addition of skin moisturizers like sodium pyrrolidone carboxylate, lactic acid and hydrolyzed collagen; preservatives like butylated toluenes, colorants and odorants, and other agents can provide further action on the skin. Such mixtures may be cast between two release liners and face masks or nail wraps die cut therefrom to the appropriate shape.

The present invention will be more readily understood from a consideration of the following specific examples which are given for the purpose of illustration only and are not to be considered as limiting in any way.

EXAMPLE I

This example illustrates the importance of ring opening in the reaction of this invention.

Twenty grams of a 20%, by weight, aqueous solution of K90 PVP which titrates with a base so that only 1.2 ml. of 0.01N NaOH is required to reach pH7 are mixed with 0.8 grams of a 25%, by weight, aqueous solution of polyethylenemine. The resulting mixture becomes more viscous but shows no evidence of gelation.

The same PVP solution is heated to 95.C. in the presence of 0.5 ml of a 1% aqueous solution of sodium hydroxide for 96 hours. Correcting for the added base, the PVP now requires 6.5 ml of 0.1N NaOH to reach pH7. When this solution is mixed with 0.8 grams of a 25% aqueous solution of polyethyleneimine, a gel is formed immediately. The gel is not soluble in water even when heated.

EXAMPLE II

Twenty grams of a 20%, by weight, aqueous solution of a commercially available ring opened PVP (K90) which requires 7.5 ml of a 0.01 N NaOH to reach pH 7 are mixed with 0.8 grams of a 25%, by weight, aqueous solution of polyethyleneimine and a gel is immediately formed. The gel is not soluble in excess added water, but does swell further.

EXAMPLE III

This example illustrates the effect of plasticizer level on tack.

To samples of 18 grams of the K90 ring opened PVP 20%, by weight, solutions as used in Example II, are added increments of polyethylene glycol 300 ranging from 1 to 6.5 grams, and 1.6 grams of a 12.5%, by weight, aqueous solution of polyethyleneimine are added to each sample. The degree of tack of the resulting gel increases as the amount of plasticizer increases, but the strength of the gel (adherence to itself) decreases above 5 grams.

EXAMPLE IV

Example III is repeated using glycerine in place of polyethylene glycol 300. The tack increases as the amount of glycerine increases, but above 6.0 grams of glycerine, while the tack remains good, gel strength is lost.

EXAMPLE V CONDUCTIVE GEL

The procedure of Example II is followed adding, however, KCl to the water before dissolving the ring opened PVP. The resulting gel, at a level of 5%, by weight, KCl has adequate conductivity for use in applications like electrocardiogram electrodes, transcutaneous electrical nerve stimulator electrodes, electro-surgical unit electrodes, bio-feedback electrodes, iontophoretic drug delivery electrodes and defibrillation pads.

EXAMPLE VI WOUND/BURN DRESSING

An aqueous solution of 30%, by weight, K90 ring opened PVP, optionally containing antimicrobial agent, is mixed with a second stream containing 2.5%, by weight, polyethyleneimine, 52.4%, by weight, polyethylene glycol and 39.8%, by weight, water. The ratio of the first solution to the second is 2:1, be weight. The solutions are introduced to a static mixing system, and 7.5 cc of the resulting material is pumped into a thermoformed plastic tray having a silicone coated lip.

A laminate having, from top to bottom, a release layer, a flexible urethane film to control moisture vapor permeability and an adhesive layer is heat sealed to the lips of the tray.

For application to a wound or burn, the tray is removed, the hydrogel dressing applied and the release layer is removed.

To the mixed solutions may be added electrolyte to match the physiological salt concentration to prevent osmotic pumping of a wound, antimicrobials to prevent bacteria growth and agents to promote regrowth of cells.

The hydrogel, by varying the amount of polyethylene glycol, can be made stringy and quite adhesive. Such modification, coupled with the inclusion of an antimicrobial, is useful in providing a antibacterial barrier around a catheter insertion into the body, for instance a central venous catheter or an intravenous catheter, thereby decreasing the possibility of bacterial infection.

EXAMPLE VII COSMETIC FACE MASK/NAIL WRAP

Two streams are mixed in a high shear mechanical mixer. One stream contains an aqueous 25%, by weight, solution of ring opened K90 PVP, 1%, by weight, sodium pyrrolidone carboxylate, cosmetic stabilizers, lactic acid and hydrolyzed collagen. The second stream 50%, by weight, polyethylene glycol 300, 44% water, 2%, by weight, polyethyleneimine and the balance phospholipid PTC surfactant and optimal materials: colorants and odorants. The streams are mixed in a weight ratio of 3 parts of the first to 1 part of the second. The resulting hydrogel is cast between two release liners on a moving conveyor. At the end of the conveyor, the laminate is die cut to the specific shape desired.

Modification is possible in the selection of additives for incorporation in the hydrogel of the present invention as well as in the method of making the hydrogel product without departing from the scope of the invention.

I claim:

1. A skin adhesive hydrogel composition comprising a water-insoluble, water-swellable cross-linked ampholyte salt of
    A. a high molecular weight water-soluble polyvinylpyrrolidone having ring opened pyrrolidone groups providing at least $1.5 \times 10^{-2}$ milliequivalents of carboxylic acid groups per gram of polymer, and
    B. a water-soluble multifinctional amine-containing polymer selected from the group consisting of polyethyleneimine, amine-terminated polyethylene oxide, amine-terminated polyethylene/polypropylene oxide, polymers of dimethyl amino ethyl methacrylate and copolymers of dimethyl amino ethyl methacrylate and vinyl pyrrolidone.

2. The composition of claim 1 wherein the multifunctional amine - containing polymer is selected from the group consisting of polyethyleneimine, amine-terminated polyethylene oxide and amine-terminated polyethylene oxide/polypropylene oxide.

3. The composition of claim 2 wherein the multifunctional amine-containing polymer is polyethyleneimine and the ratio, by weight, of polyvinyl pyrrolidone to polyethyleneimine is from about 15:1 to about 40:1.

4. The composition of claim 1 wherein the ring opened polyvinylpyrrolidone has a K-value of at least about 50.

5. The composition of claim 1 comprising also a plasticizer for the hydrogel.

6. The composition of claim 5 wherein the plasticizer is selected from the group consisting of glycerine, ethylene glycol, polypropylene glycol and polyethylene glycol.

7. In a system for attachment to the skin of animals including humans, for cosmetic or medical purposes and including a skin adhesive hydrogel, a plasticizer therefor and a component adapted to impart the desired cosmetic or medical result to or through the skin, the improvement wherein the skin adhesive hydrogel comprises the composition of claim 1.

8. The system of claim 7 in the form of a wound or burn dressing or packing comprising a polymeric film backing controlling the moisture-vapor-transmission rate and wherein the component adopted to impart the desired medical effect is an antimicrobial agent.

9. The system of claim 7 in the form of an electrically conductive electrode adhesive agent wherein the component adapted to provide the desired medical effect is an electrolyte salt.

10. The system of claim 7 in the form of an adhesive agent for attaching a catheter hub or ostomy product to the skin wherein the component adapted to provide the desired medical effect is an antimicrobial agent.

11. The system of claim 9 comprising also an iontophoretic drug.

12. The system of claim 7 in the form of a face mask or nail wrap wherein the component adapted to provide the desired cosmetic effect is a skin moisturizing agent.

13. The system of claim 7 comprising also a transdermal drug.

14. The system of claim 13 comprising also a skin adsorption enhancing agent.

15. The method of making a polymer for skin adhesive hydrogel which comprises mixing in aqueous medium
  A. a high molecular weight water-soluble polyvinylpyrrolidone having ring opened pyrrolidone groups providing at least $1.5 \times 10$ milliequivalents of carboxylic acid groups per gram of polymer, and
  B. a water-soluble multifunctional amine-containing polymer selected from the group consisting of polyethyleneimine, amine terminated polyethylene oxide, amine terminated polyethylene/polypropylene oxide, polymers of dimethyl amino ethyl methacrylate and copolymers of dimethyl amino ethyl methacrylate and vinyl pyrrolidone until reaction between acid groups of the ring opened polyvinyl-pyrrolidone and basic amine groups of the water-soluble multifunctional amine-containing polymer form a water-insoluble, water-swellable cross-linked ampholyte salt.

16. The method of claim 15 wherein the multifunctional amine-containing polymer is selected from the group consisting of polyethyleneimine, amine-terminated polyethylene oxide and amine-terminated polyethylene oxide/polypropylene oxide.

17. The method of claim 16 wherein the multifunctional amine-containing polymer comprises polyethyleneimine and the ratio, by weight, of polyvinyl pyrrolidone to polyethyleneimine is from about 15:1 to about 40:1.

18. The method of claim 14 wherein the ring opened polyvinylpyrrolidone has a K-value of at least about 50.

19. The method of claim 14 wherein the water content of the reaction mixture is from about 40 to about 75%, by weight.

20. The method of claim 14 wherein the reaction is conducted in the presence of a plasticizer.

21. The method of claim 20 wherein the plasticizer is selected from the group consisting of glycerine, ethylene glycol, polypropylene glycol and polyethylene glycol.

22. The method of claim 20 wherein the amount of plasticizer in the reaction mixture is from about 1 to about 30%, by weight, based on the total reaction mixture.

* * * * *

UNITED STATES PATENT AND TRADEMARK OFFICE
CERTIFICATE OF CORRECTION

PATENT NO. : 5,306,504
DATED : April 26, 1994
INVENTOR(S) : Donald H. Lorenz

It is certified that error appears in the above-indentified patent and that said Letters Patent is hereby corrected as shown below:

On the title page, Item [73]: Assignee, "Paper Manufactures Company" should read --Paper Manufacturers Company--;

Column 5, line 3, "95.C." should read --95°C--;

Column 6, line 42, "milliequivalents" should read -- milli-equivalents--.

Signed and Sealed this

Twenty-seventh Day of September, 1994

Attest:

BRUCE LEHMAN

*Attesting Officer*  *Commissioner of Patents and Trademarks*